United States Patent
Gu et al.

(10) Patent No.: US 10,568,606 B2
(45) Date of Patent: Feb. 25, 2020

(54) ULTRASONIC PROBE AND METHOD OF MANUFACTURING THE SAME

(71) Applicant: SAMSUNG MEDISON CO., LTD., Hongcheon-gun, Gangwon-do (KR)

(72) Inventors: Jin Ho Gu, Hwaseong-si (KR); Jae-Yk Kim, Seongnam-si (KR); Jong Mok Lee, Yongin-si (KR); Young Mun Cho, Seoul (KR)

(73) Assignee: Samsung Medison Co., Ltd., Hongcheon-gun, Gangwon-do (KR)

(*) Notice: Subject to any disclaimer, the term of this patent is extended or adjusted under 35 U.S.C. 154(b) by 951 days.

(21) Appl. No.: 14/956,340

(22) Filed: Dec. 1, 2015

(65) Prior Publication Data

US 2016/0151043 A1 Jun. 2, 2016

(30) Foreign Application Priority Data

Dec. 2, 2014 (KR) .................. 10-2014-0170646
Mar. 3, 2015 (KR) .................. 10-2015-0029990

(51) Int. Cl.
*A61B 8/00* (2006.01)

(52) U.S. Cl.
CPC .......... *A61B 8/4444* (2013.01); *A61B 8/4494* (2013.01)

(58) Field of Classification Search
CPC ... A61B 8/4444; A61B 8/4494; B06B 1/0622; H01L 41/29; H01L 41/0475

(Continued)

(56) References Cited

U.S. PATENT DOCUMENTS

| | | | |
|---|---|---|---|
| 6,625,854 B1* | 9/2003 | Sudol | B06B 1/0662 29/25.35 |
| 2004/0095045 A1* | 5/2004 | Baumgartner | B06B 1/06 310/365 |

(Continued)

FOREIGN PATENT DOCUMENTS

| | | |
|---|---|---|
| CN | 101199434 A | 6/2008 |
| CN | 101238506 A | 8/2008 |

(Continued)

OTHER PUBLICATIONS

Partial European Search Report issued in corresponding European Patent Application No. 15193197.9, dated May 4, 2016.

(Continued)

*Primary Examiner* — Sanjay Cattungal
(74) *Attorney, Agent, or Firm* — Morgan, Lewis & Bockius LLP

(57) ABSTRACT

An ultrasonic probe includes a connection layer including a conductor array for connecting a transducer array and a printed circuit board (PCB) to an application specific integrated circuit (ASIC). The ultrasonic probe includes a transducer array which transmits and receives an ultrasonic wave, a first electronic circuit electrically connected to the transducer array, a second electronic circuit electrically connected to the first electronic circuit, and a connection layer disposed between the transducer array and the first electronic circuit and including a first conductor array in contact with the transducer array so that the transducer array is electrically connected to the first electronic circuit and a second conductor array in contact with the second electronic circuit so that the second electronic circuit is electrically connected to the first electronic circuit.

33 Claims, 12 Drawing Sheets

(58) Field of Classification Search
USPC .................................................. 600/437–469
See application file for complete search history.

(56) References Cited

U.S. PATENT DOCUMENTS

| | | | | |
|---|---|---|---|---|
| 2004/0100163 | A1* | 5/2004 | Baumgartner | B06B 1/0622 310/334 |
| 2006/0184035 | A1* | 8/2006 | Kimura | A61B 8/12 600/466 |
| 2007/0046149 | A1* | 3/2007 | Zipparo | B06B 1/0629 310/334 |
| 2007/0164632 | A1* | 7/2007 | Adachi | A61B 8/4483 310/311 |
| 2008/0134793 | A1* | 6/2008 | Woychik | B06B 1/0292 73/649 |
| 2013/0241355 | A1* | 9/2013 | Okada | B06B 1/0622 310/334 |
| 2013/0281857 | A1* | 10/2013 | Ko | B06B 1/0629 600/443 |
| 2015/0018687 | A1* | 1/2015 | Osawa | B06B 1/0622 600/459 |

FOREIGN PATENT DOCUMENTS

| | | |
|---|---|---|
| CN | 102218394 A | 10/2011 |
| CN | 103635264 A | 3/2014 |
| WO | 2007/017776 A2 | 2/2007 |
| WO | 2007017776 A2 | 2/2007 |
| WO | 2013/001448 A1 | 1/2013 |

OTHER PUBLICATIONS

Extended European Search Report issued in corresponding European Patent Application No. 15193197.9, dated Sep. 9, 2016.
Chinese Office Action dated Sep. 3, 2019 issued in Chinese Patent Application No. 201510872799.8 (with English translation).

* cited by examiner

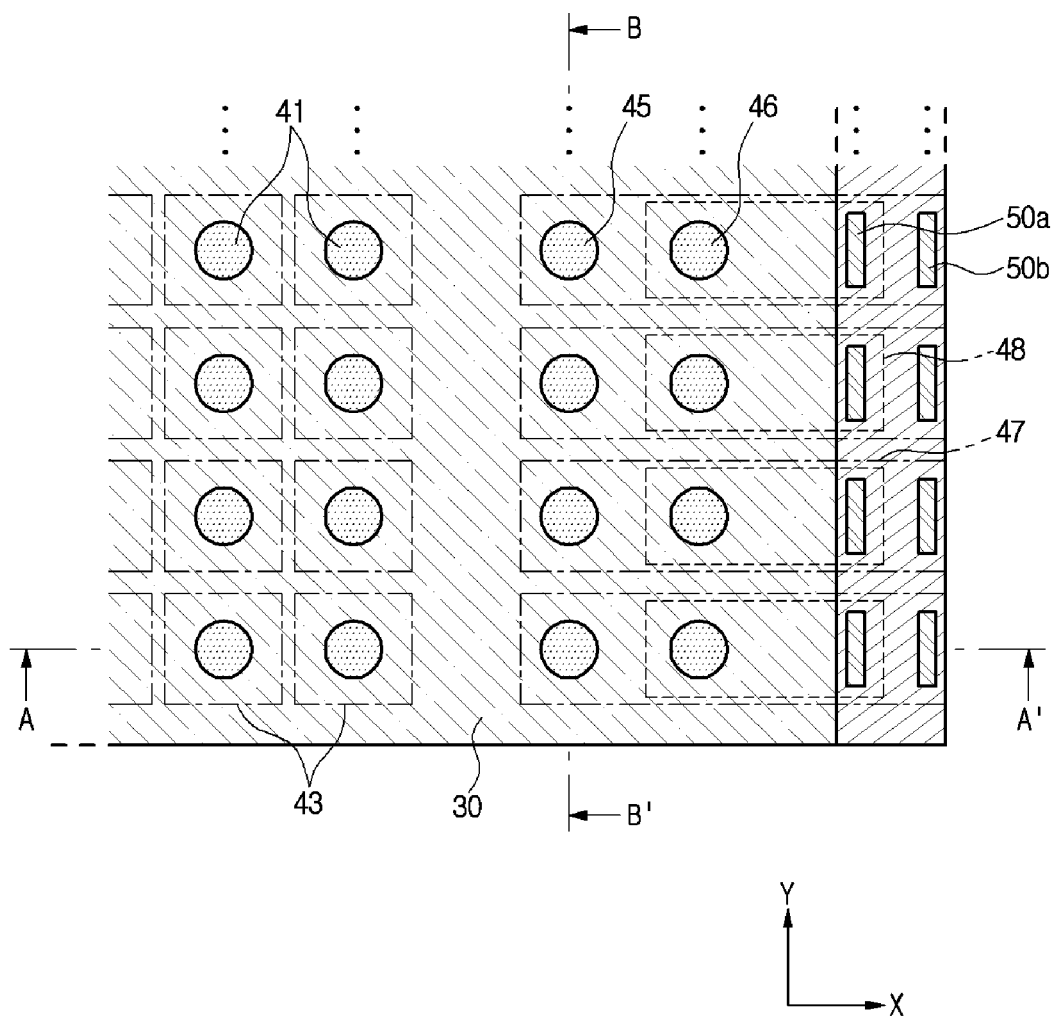

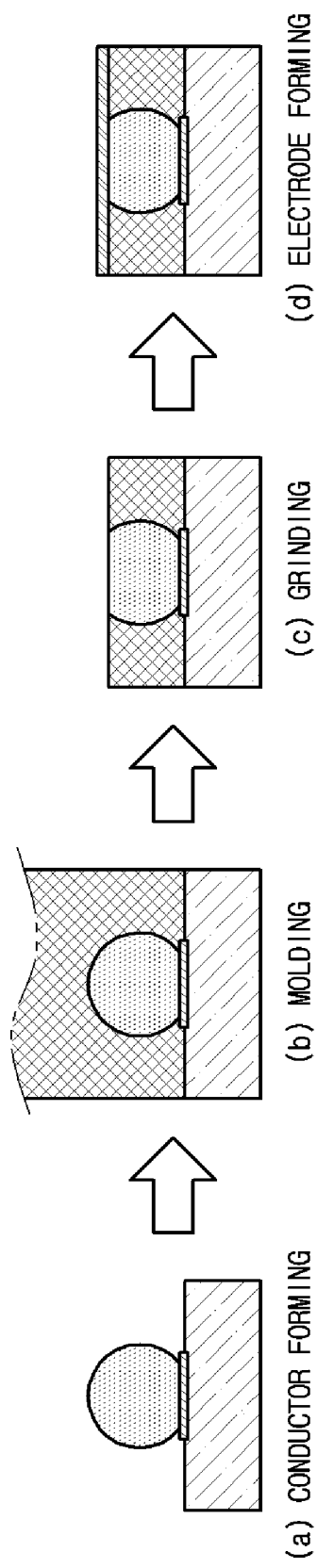

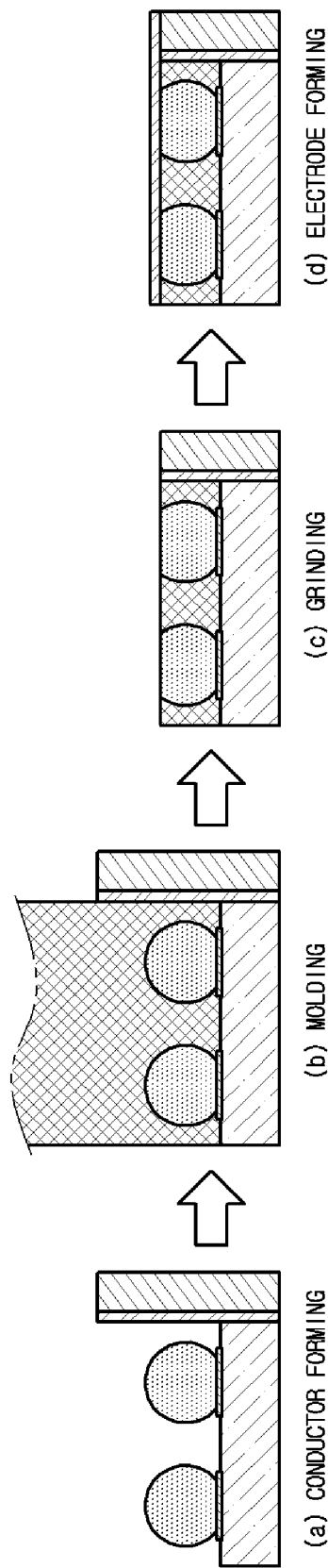

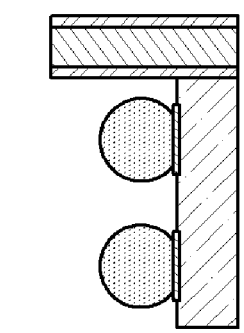
FIG. 11A (a) CONDUCTOR FORMING
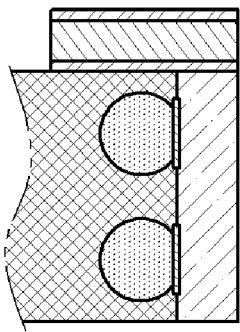
FIG. 11B (b) MOLDING
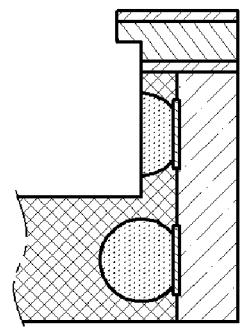
FIG. 11C (c) GRINDING
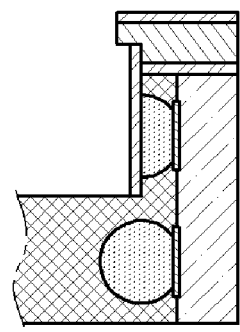
FIG. 11D (d) ELECTRODE FORMING
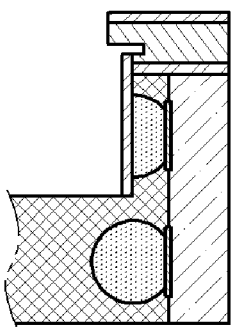
FIG. 11E (e) ELECTRODE SEPARATING
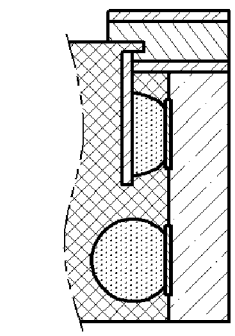
FIG. 11F (f) MOLDING
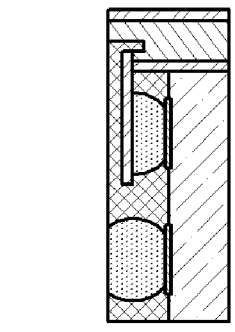
FIG. 11G (g) GRINDING
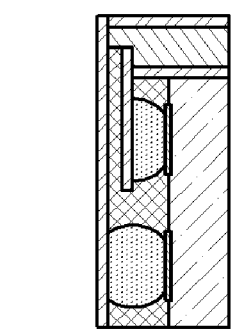
FIG. 11H (h) ELECTRODE FORMING

ULTRASONIC PROBE AND METHOD OF MANUFACTURING THE SAME

CROSS-REFERENCE TO RELATED APPLICATIONS

This application claims the benefit of Korean Patent Application No. 10-2014-0170646 and 10-2015-0029990, filed on Dec. 2, 2014 and Mar. 3, 2015, respectively, in the Korean Intellectual Property Office, the disclosure of which is incorporated herein by reference.

TECHNICAL FIELD

Embodiments of the present invention relate to an ultrasonic probe for generating an interior image of an object using an ultrasonic wave.

BACKGROUND

An ultrasonic imaging apparatus may radiate an ultrasonic signal toward a target area inside a body from a body surface of an object and obtain a tomogram of a soft tissue or an image of a blood flow in a non-invasive manner using information on a reflected ultrasonic signal (ultrasonic echo signal).

Ultrasonic imaging apparatuses are advantageous, because they are small, cheap, can display images in real time, and are very safe due to no exposure to X-rays, compared to other image diagnostic apparatuses such as X-ray diagnostic apparatuses, X-ray computerized tomography (CT) scanners, magnetic resonance imaging (MRI) apparatuses, and nuclear medicine diagnostic apparatuses, etc. Therefore, the ultrasonic imaging apparatuses are being widely used for heart, abdomen, urinary tract, and ob/gyn diagnoses.

In general, an ultrasonic imaging apparatus transmits an ultrasonic signal to the object in order to obtain an ultrasonic image of the object, and includes an ultrasonic probe for receiving an ultrasonic echo signal reflected from the object and a main device for generating interior images of the object using the ultrasonic echo signal received from the ultrasonic probe.

SUMMARY

Therefore, it is an aspect of the present invention to provide an ultrasonic probe including a connection layer in which a conductor array for connecting a transducer array and a printed circuit board (PCB) to an application specific integrated circuit (ASIC) is included.

Additional aspects of the invention will be set forth in part in the description which follows and, in part, will be obvious from the description, or may be learned by practice of the invention.

In accordance with one aspect of the present invention, an ultrasonic probe includes a transducer which transmits and receives an ultrasonic wave, a first electronic circuit electrically connected to the transducer, second electronic circuits each electrically connected to the first electronic circuit, and a connection layer including a first conductor disposed between the transducer and the first electronic circuit so that the transducer is electrically connected to the first electronic circuit and a second conductor disposed on one surface of the first electronic circuit so that the second electronic circuit is electrically connected to the first electronic circuit.

The ultrasonic probe may further include an electrode disposed on a front surface of the connection layer to be in contact with the first conductor and the transducer.

The ultrasonic probe may further include an electrode disposed on a front surface of the connection layer to be in contact with the second conductor and the second electronic circuit.

The second electronic circuit may be disposed on a surface adjacent to the second conductor among side surfaces of the first electronic circuit, and the second conductor may include a plurality of columns formed in a direction parallel to the second electronic circuit, and an electrode which connects any one column of the second conductor to any one second electronic circuit and an electrode which connects another column of the second conductor to another second electronic circuit are spaced apart from each other.

The plurality of columns of the second conductor may be formed in the same layer.

The electrode which connects any one column of the second conductor to any one second electronic circuit and the electrode which connects another column of the second conductor to another second electronic circuit may be formed in different layers.

An area of the electrode may be provided to correspond to an area of the transducer being in contact with the electrode.

The electrode may have a thickness in a range from 0.1 μm to 5 μm.

The electrode may be formed using a sputtering method or a plating method.

The first conductor and the second conductor may be formed in the same layer.

At least one of the first electronic circuit and the second electronic circuit may include a semiconductor device (an application specific integrated circuit (ASIC)).

The connection layer may be disposed on a back surface of the transducer, the first electronic circuit may be disposed on a back surface of the connection layer, and the second electronic circuit may be disposed on a side surface of the first electronic circuit.

The transducer may be formed in an array form including a plurality of elements and the first conductor may be formed in an array form including a plurality of conductors.

The connection layer may include a non-conductive material which embeds the first conductor and the second conductor.

In accordance with another aspect of the present invention, an ultrasonic probe includes a transducer which transmits and receives an ultrasonic wave, a connection layer disposed on a back surface of the transducer and electrically connected to the transducer, a first electronic circuit disposed on a back surface of the connection layer to be electrically connected to the connection layer, and a second electronic circuit disposed on a side surface of the first electronic circuit to be electrically connected to the first electronic circuit. The connection layer includes a first conductor disposed between the transducer and the first electronic circuit so that the transducer is electrically connected to the first electronic circuit, and a second conductor disposed on a front surface of the first electronic circuit so that the first electronic circuit is electrically connected to the second electronic circuit.

In accordance with still another aspect of the present invention, an ultrasonic probe includes a transducer which transmits and receives an ultrasonic wave, a first conductor disposed on a back surface of the transducer, a first electrode disposed between the transducer and the first conductor so that the transducer is electrically connected to the first conductor, a first electronic circuit disposed on a back surface of the first conductor to be electrically connected to the first conductor, a second conductor disposed on a front surface of the first electronic circuit to be electrically connected to the first electronic circuit, a second electrode disposed on a front surface of the second conductor, and a second electronic circuit disposed on a side surface of the first electronic circuit and electrically connected to the second electrode.

In accordance with yet another aspect of the present invention, an ultrasonic probe includes a transducer which transmits and receives an ultrasonic wave, a first electronic circuit electrically connected to the transducer and a connection layer disposed between the transducer and the first electronic circuit. The connection layer is disposed between the transducer and the first electronic circuit so that the transducer is electrically connected to the first electronic circuit.

The ultrasonic probe may further include an electrode disposed on a front surface of the connection layer to be in contact with the first conductor and the transducer.

The electrode may have a thickness in a range from 0.1 μm to 5 μm.

The electrode may be formed using a sputtering method or a plating method.

The first electronic circuit may include a semiconductor device (ASIC).

In accordance with yet another aspect of the present invention, an ultrasonic probe includes a transducer which transmits and receives an ultrasonic wave, a first electronic circuit electrically connected to the transducer, a connection layer disposed between the transducer and the first electronic circuit, and second electronic circuits each disposed on a side surface of the first electronic circuit to be electrically connected to the first electronic circuit. The connection layer includes a second conductor disposed on a front surface of the first electronic circuit so that the second electronic circuit is electrically connected to the first electronic circuit.

The ultrasonic probe may further include an electrode disposed on a front surface of the connection layer to be in contact with the second conductor and the second electronic circuit.

The second electronic circuit may be disposed on a surface adjacent to the second conductor among side surfaces of the first electronic circuit, and the second conductor may include a plurality of columns formed in a direction parallel to the second electronic circuit, and an electrode which connects any one column of the second conductor to any one second electronic circuit and an electrode which connects another column of the second conductor to another second electronic circuit are spaced apart from each other.

The plurality of columns of the second conductor may be formed in the same layer.

The electrode which connects any one column of the second conductor to any one second electronic circuit and the electrode which connects another column of the second conductor to another second electronic circuit may be formed in different layers.

In accordance with yet another aspect of the present invention, a method of manufacturing an ultrasonic probe includes forming a conductor array on one surface of a first electronic circuit, molding a space including the conductor array, performing a grinding process on the molding to expose the conductor array, forming an electrode on a surface on which the grinding process is performed, and stacking a transducer on the electrode.

The method may further include performing a dicing process on the transducer and the molding so that the transducer is formed as a 2-dimensional (2D) array.

The forming of the electrode may include forming an electrode on the exposed conductor array and the molding therearound through a sputtering method or a plating method.

The forming of the electrode may include forming an electrode having a thickness in a range from 0.1 μm to 5 μm on the exposed conductor array through a sputtering method or a plating method.

The method may further include installing at least one second electronic circuit on one side surface of the first electronic circuit. The forming of the conductor array may include forming a first conductor array connected to the transducer and a second conductor array connected to the at least one second electronic circuit.

The forming of the electrode may include forming an electrode on the exposed first conductor array and second conductor array, the molding around the first and second conductor arrays, and the at least one second electronic circuit through a sputtering method.

The method, when the transducer is stacked on the electrode formed on the first conductor array, may further include dicing the transducer and the molding in a direction perpendicular to the at least one second electronic circuit, and dicing the transducer and the molding corresponding to the transducer in a direction perpendicular to the dicing direction and generating a 2D array transducer.

The second conductor array may include a plurality of columns formed in a direction parallel to the at least one second electronic circuit, and the performing of the grinding process may further include performing a grinding process on the molding corresponding to any one column of the plurality of columns of the second conductor array and any one second electronic circuit among the at least one second electronic circuit, and the forming of the electrode may include forming an electrode on a surface on which the grinding process is performed through a sputtering method so that the any one column of the second conductor array exposed by performing the grinding process is electrically connected to the at least one second electronic circuit.

The method may further include cutting an end of the formed electrode at a side of the second electronic circuit in order to prevent the formed electrode and another electronic circuit from being electrically connected, remolding the electrode, further performing a grinding process on the molding corresponding to another column so that another column of the plurality of columns of the second conductor array is further exposed, and further forming an electrode on a surface on which the grinding process is further performed through a sputtering method so that another column of the plurality of columns of the second conductor array is electrically connected to another second electronic circuit of the at least one second electronic circuit.

In accordance with yet another aspect of the present invention, an ultrasonic probe includes an ultrasonic transducer including one or more ultrasonic transducer elements, a first electronic circuit including one or more pads that correspond to the one or more ultrasonic transducer elements and extend along a first direction, a connection layer interposed between the ultrasonic transducer and the first electronic circuit, and including one or more first conductors electrically connecting the one or more ultrasonic transducer elements and the one or more pads to each other and an electrically insulating layer filling spaces around the one or more first conductors, a second electronic circuit disposed on a side surface of the first electronic circuit by extending along a second direction intersected by the first direction, and electrically connected to the first electronic circuit via an electrode extending along the first direction.

The ultrasonic probe may further include one or more first electrodes interposed between the one or more first conductors and the one or more ultrasonic transducer elements.

The electrically insulating layer may have one or more grooves adjacent to the one or more first conductors. A side wall of each groove may be coplanar with side surfaces of one first electrode and one ultrasonic transducer element.

The electrode, via which the first electronic circuit and the second electronic circuit are electrically connected to each other, may be coplanar with the one or more first electrodes.

The ultrasonic probe may further include an embedded electrode embedded within the electrically insulating layer of the connection layer. The second electronic circuit may include an electrically insulating separator and first and second electronic layers that are disposed on opposite surfaces of the electrically insulating separator and that are electrically connected to the electrode and the embedded electrode, respectively.

The first and second electronic layers of the second electronic circuit may be printed circuit boards.

The electrode may have a thickness in a range from 0.1 μm to 5 μm.

At least one of the first electronic circuit and the second electronic circuit may be a semiconductor chip.

BRIEF DESCRIPTION OF THE DRAWINGS

These and/or other aspects of the invention will become apparent and more readily appreciated from the following description of the embodiments, taken in conjunction with the accompanying drawings of which:

FIG. 5 is a plan view conceptually showing a connection layer of an ultrasonic probe according to an embodiment of the present invention;

FIGS. 9A-9D are cross-sectional views conceptually showing a process of forming an electrode on a conductor array included in a connection layer of an ultrasonic probe according to an embodiment of the present invention;

FIGS. 10A-10D are cross-sectional views conceptually showing a process of forming an electrode when a second conductor array configured in a single column is included in a connection layer of an ultrasonic probe according to an embodiment of the present invention; and FIGS. 11A-11H are cross-sectional views conceptually showing a process of forming an electrode when a second conductor array configured in two columns is included in a connection layer of an ultrasonic probe according to an embodiment of the present invention.

DETAILED DESCRIPTION

Figure 1:
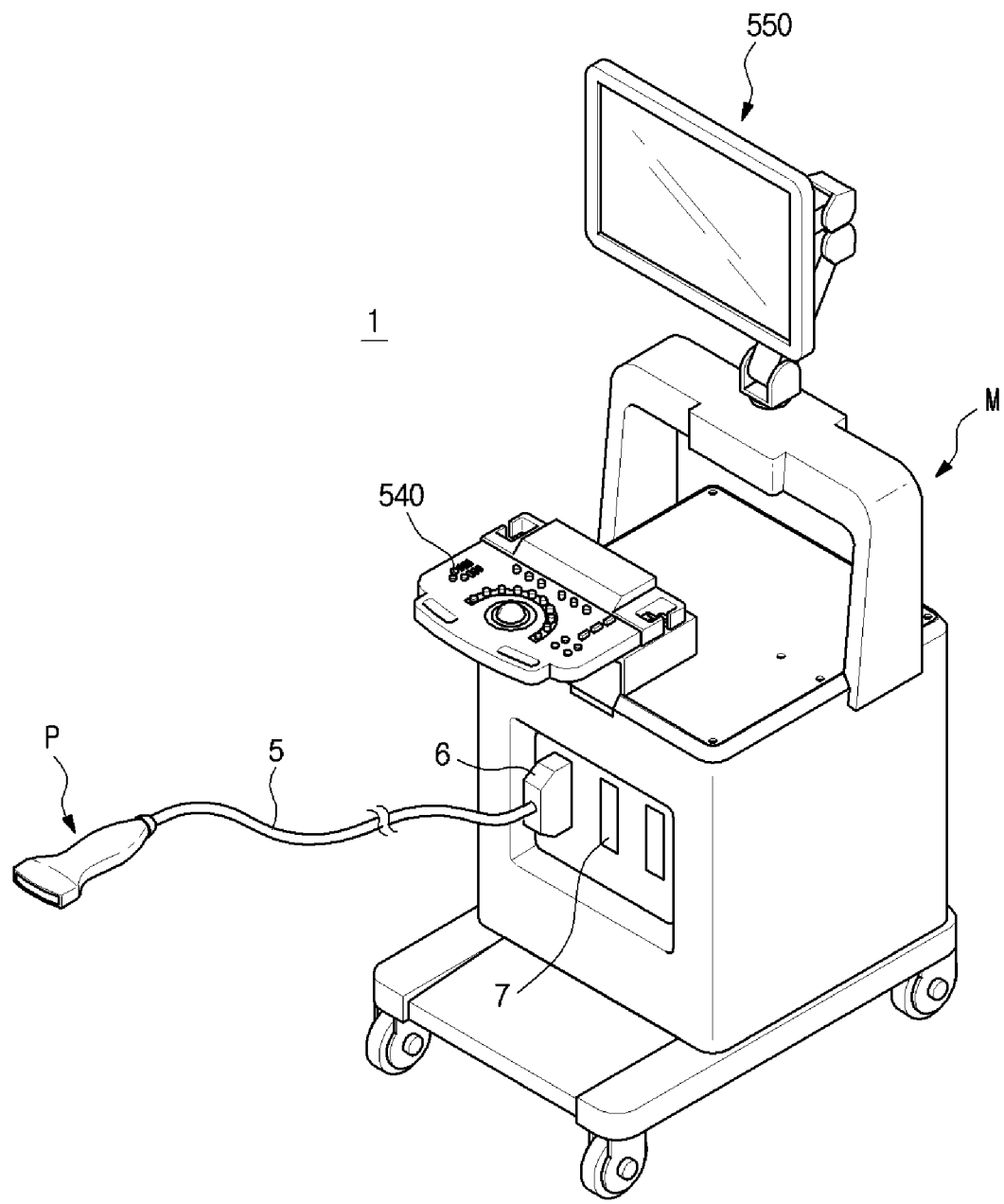
FIG. 1 is a diagram schematically showing an exterior of an ultrasonic imaging apparatus according to an embodiment of the present invention.

Reference will now be made in detail to the embodiments of the present invention, examples of which are illustrated in the accompanying drawings, wherein like reference numerals refer to like elements throughout.

Hereinafter, embodiments will be described in detail with reference to the accompanying drawings.

Figure 2:
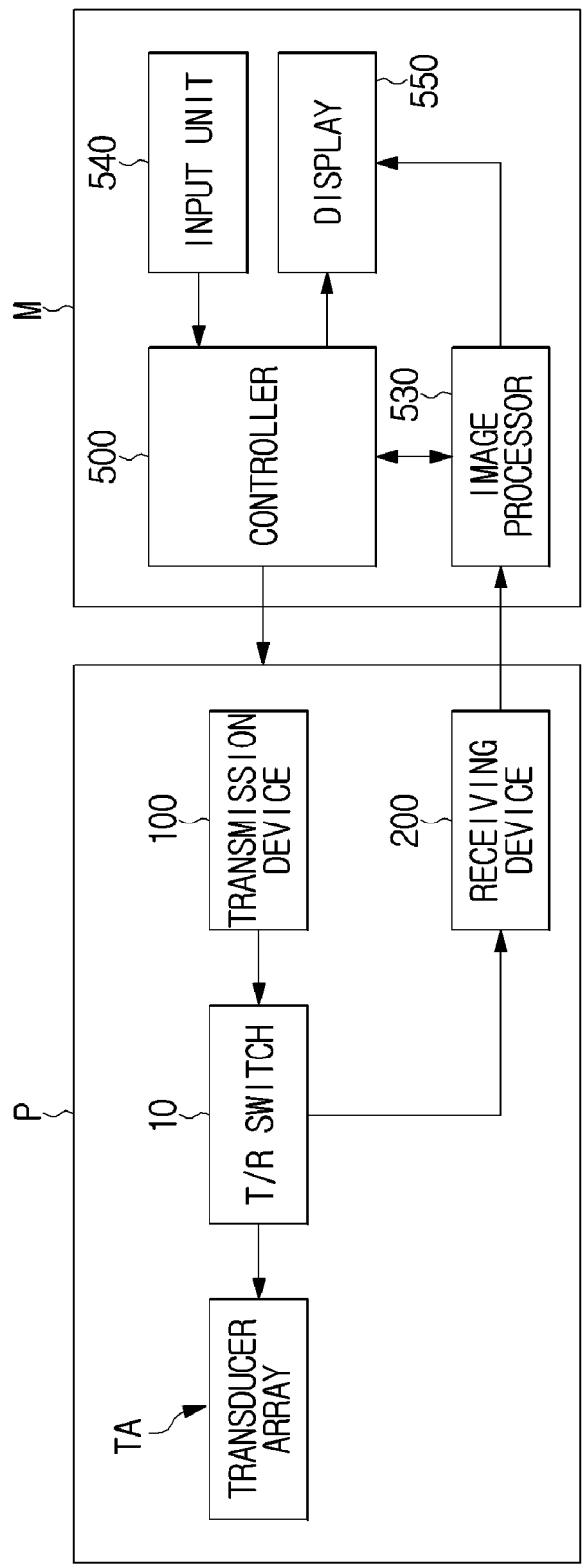
FIG. 2 is a control block diagram showing an ultrasonic imaging apparatus according to an embodiment of the present invention.
Figure 3:
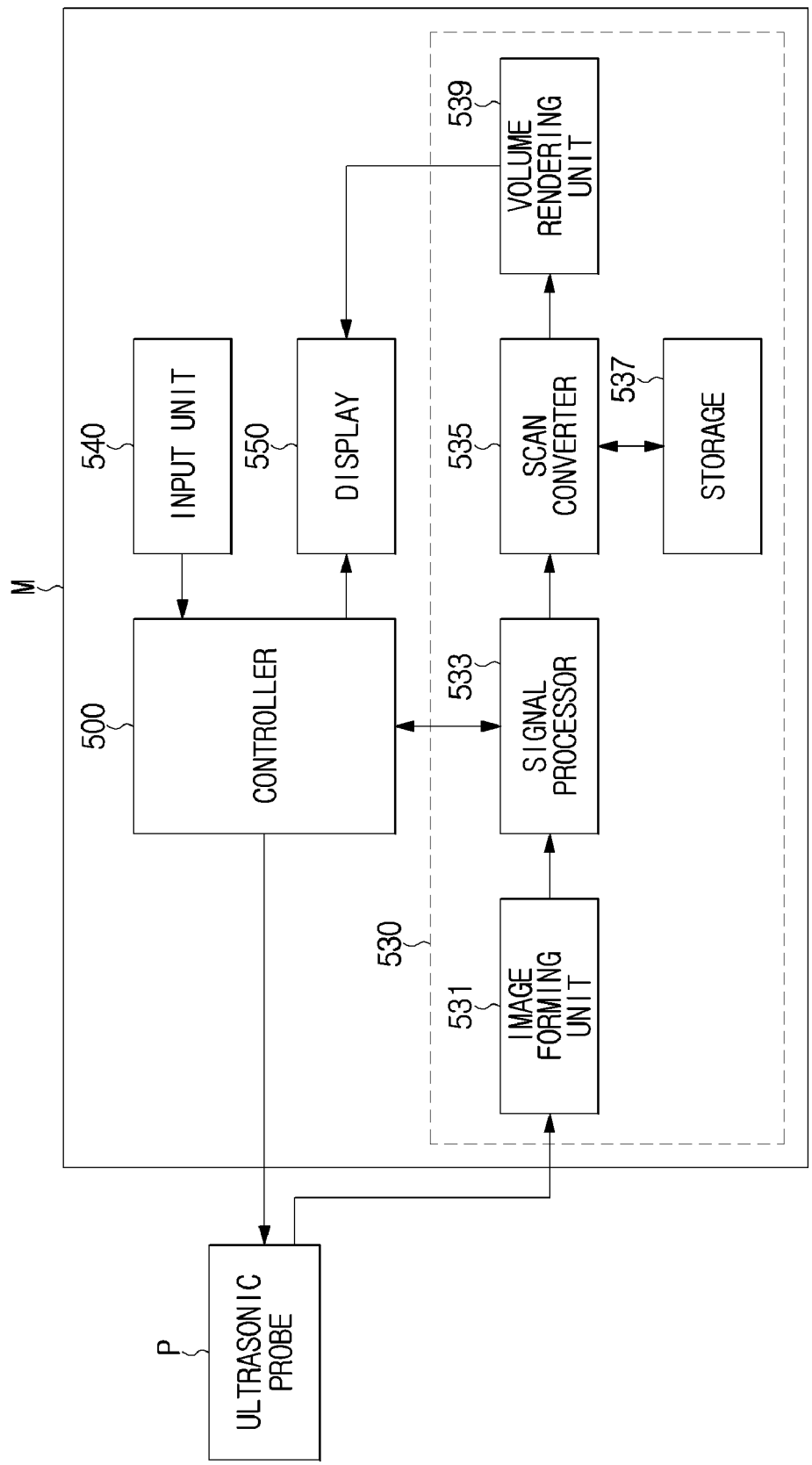
FIG. 3 is a control block diagram showing a configuration of a main device of an ultrasonic imaging apparatus according to an embodiment of the present invention.

FIG. 1 is a diagram schematically showing an exterior of an ultrasonic imaging apparatus according to an embodiment of the present invention. FIG. 2 is a control block diagram showing an ultrasonic imaging apparatus according to an embodiment of the present invention. FIG. 3 is a control block diagram showing a configuration of a main device of an ultrasonic imaging apparatus according to an embodiment of the present invention.

Referring to FIG. 1, an ultrasonic imaging apparatus 1 includes an ultrasonic probe P which transmits an ultrasonic wave to an object, receives an ultrasonic echo signal from the object, and converts the ultrasonic echo signal into an electrical signal, and a main device M which is connected to the ultrasonic probe P, includes an input unit 540 and a display 550, and displays an ultrasonic image. The ultrasonic probe P is connected to the main device M of the ultrasonic imaging apparatus through a cable 5, and may receive various signals necessary for controlling the ultrasonic probe P or deliver an analog signal or a digital signal corresponding to the ultrasonic echo signal received by the ultrasonic probe P to the main device M. However, the embodiment of the ultrasonic probe P is not limited thereto, and a wireless probe may be implemented to transmit and receive a signal via a wireless network formed between the ultrasonic probe P and the main device M.

One end of the cable 5 is connected to the ultrasonic probe P, and a connector 6 detachable from a slot 7 of the main device M may be provided at the other end of the cable 5. The main device M and the ultrasonic probe P may transmit and receive a control command or data using the cable 5. For example, when a user inputs information on a focal depth, a size or a shape of an aperture, a steering angle, or the like through the input unit 540, the information may be delivered to the ultrasonic probe P through the cable 5 and used for transceiver beamforming of a transmission device 100 and a receiving device 200. Also, as described above, when the ultrasonic probe P is implemented as the wireless probe, the ultrasonic probe P is connected to the main device M via a wireless network without the cable 5. When the ultrasonic probe P is connected to the main device M via the wireless network, the main device M and the ultrasonic probe P may transmit and receive the above-described control command or data. As shown in FIG. 2, the main device M may include a controller 500, an image processor 530, the input unit 540, and the display 550.

The controller 500 controls overall operations of the ultrasonic imaging apparatus 1. Specifically, the controller 500 generates a control signal for controlling each component of the ultrasonic diagnostic apparatus 1, for example, the transmission device 100, a transmitting/receiving (T/R) switch 10, the receiving device 200, the image processor 530, the display 550, or the like shown in FIG. 2, and controls an operation of each of the above-described components. In the ultrasonic imaging apparatus 1 according to the embodiment of the present invention shown in FIGS. 2 and 3, the transceiving beamformer is included in the ultrasonic probe P rather than in the main device M; however, according other embodiments, the transceiving beamformer may be included in the main device M rather than in the ultrasonic probe P.

The controller 500 generates a delay profile of a plurality of ultrasonic transducer elements 60 (shown in FIGS. 4A and 4B) of a ultrasonic transducer array TA, and calculates a time delay value resulting from a distance difference between the plurality of ultrasonic transducer elements 60 included in the ultrasonic transducer array TA array and a focal point of the object based on the generated delay profile. Also, the controller 500 controls the transceiving beamformer to generate a transceiving signal according to the time delay value.

Also, the controller 500 may generate a control command for each of the components of the ultrasonic diagnostic apparatus 1 according to the user's instruction or command input through the input unit 540 to control the ultrasonic diagnostic apparatus 1.

The image processor 530 generates an ultrasonic image of a target area inside the object based on an ultrasonic signal focused through the receiving device 200.

Referring to FIG. 3, the image processor 530 may include an image forming unit 531, a signal processor 533, a scan converter 535, a storage 537, and a volume rendering unit 539.

The image forming unit 531 generates a coherent 2-dimensional (2D) image or 3D image of the target area inside the object based on the ultrasonic signal gathered through the receiving device 200.

The signal processor 533 converts coherent image information formed by the image forming unit 531 into ultrasonic image information according to a diagnostic mode such as a brightness mode (B-mode) or a Doppler mode (D-mode). For example, when the diagnostic mode is set to the B-mode, the signal processor 533 performs a process such as an analog-to-digital (A/D) converting process, and generates ultrasonic image information for a B-mode image in real time. Also, when the diagnostic mode is set to a D-mode, the signal processor 533 extracts phase shift information from the ultrasonic signal, calculates information on a blood flow corresponding to each point of cross sections to be imaged such as a speed, power, and a distribution, and generates ultrasonic image information for a D-mode image in real time.

The scan converter 535 converts the converted ultrasonic image information input from the signal processor 533 or the converted ultrasonic image information stored in the storage 537 into a general image signal for the display 550, and transmits the result to the volume rendering unit 539.

The storage 537 temporarily or permanently stores the ultrasonic image information that was converted through the scan converter 535.

The volume rendering unit 539 performs volume rendering based on the image signal transmitted from the scan converter 535, compensates for the rendered image information, generates the final result image, and then transmits the generated result image to the display 550.

The input unit 540 is provided for the user to input a command for an operation of the ultrasonic diagnostic apparatus 1. The user may input or set an ultrasonic diagnosis starting command, a diagnostic mode select command such as an amplitude mode (A-mode), a B-mode, a color mode, a D-mode, and a motion mode (M-mode), and region of interest (ROI) setting information including a size and a position of the ROI through the input unit 540. The input unit 540 includes various components such as a keyboard, a mouse, a trackball, a tablet, or a touch screen module that may be used by the user to input data or an instruction or command.

The display 550 displays menus or instructions necessary for ultrasonic diagnosis, an ultrasonic image obtained by an ultrasonic diagnostic process, etc. The display 550 displays an ultrasonic image of the target area inside the object generated by the image processor 530. The ultrasonic image displayed on the display 550 may be an ultrasonic image in the A-mode, an ultrasonic image in the B-mode, or a 3D stereoscopic ultrasonic image. The display 550 may be implemented in various known display methods by a component such as a cathode ray tube (CRT) or a liquid crystal display (LCD).

As illustrated in FIG. 2, the ultrasonic probe P according to the embodiment may include a transducer array TA, a T/R switch 10, a transmission device 100, and a receiving device 200. The transducer array TA is provided on an end of the ultrasonic probe P. The ultrasonic transducer array TA refers to a plurality of ultrasonic transducer elements 60 that are disposed in the form of a 1D array or a 2D array. The ultrasonic transducer array TA vibrates due to a pulse signal or alternating current (AC current) applied thereto and generates an ultrasonic wave. The generated ultrasonic wave is transmitted to the target area inside the object. In this case, the ultrasonic wave generated in the ultrasonic transducer array TA may be focused on and transmitted to a plurality of target areas inside the object. That is, the generated ultrasonic wave may be multi-focused on and transmitted to the plurality of target areas.

The ultrasonic wave generated in the ultrasonic transducer array TA is reflected from the target area inside the object and is returned to the ultrasonic transducer array TA. The ultrasonic transducer array TA receives an ultrasonic echo signal that is reflected back from the target area. When the ultrasonic echo signal arrives at the ultrasonic transducer array TA, the ultrasonic transducer array TA vibrates at a predetermined frequency corresponding to a frequency of the ultrasonic echo signal, and outputs AC current of a frequency corresponding to a vibration frequency of the ultrasonic transducer array TA. Therefore, the ultrasonic transducer array TA may convert the received ultrasonic echo signal into a predetermined electrical signal. Since each of the elements 60 receives the ultrasonic echo signal and outputs an electrical signal, the ultrasonic transducer array TA may output electrical signals of a plurality of channels.

The ultrasonic transducer may be implemented as one of a magnetostrictive ultrasonic transducer using a magnetostrictive effect of a magnetic material, a piezoelectric ultrasonic transducer using a piezoelectric effect of a piezoelectric material, and a capacitive micromachined ultrasonic transducer (cMUT) that transmits and receives an ultrasonic wave using vibrations of several hundreds or thousands of micromachined thin films. Also, other types of transducers capable of generating an ultrasonic wave according to an electrical signal or an electrical signal according to the ultrasonic wave may be exemplary ultrasonic transducers.

For example, the ultrasonic transducer element 60 according to the embodiment of the present invention may include a piezoelectric vibrator or a thin film. When AC current is applied from a power source, the piezoelectric vibrator or the thin film vibrates at a predetermined frequency according to the applied AC current, and generates an ultrasonic wave of a predetermined frequency according to the vibration frequency. On the other hand, when the ultrasonic echo signal of a predetermined frequency arrives at the piezoelectric vibrator or the thin film, the piezoelectric vibrator or the thin film vibrates according to the ultrasonic echo signal, and outputs AC current of a frequency corresponding to the vibration frequency.

The transmission device 100 applies a transmitting pulse to the transducer array TA, and enables the transducer array TA to transmit the ultrasonic signal to the target area inside the object. The transmission device 100 may include a transmitting beamformer and a pulser.

The transmitting beamformer forms a transmission signal pattern according to a control signal of the controller 500 of the main device M, and outputs the formed transmission signal pattern to the pulser. The transmitting beamformer forms the transmission signal pattern based on a time delay value of each of the ultrasonic transducer elements 60 that constitute the ultrasonic transducer array TA, which is calculated through the controller 500, and transmits the formed transmission signal pattern to the pulser.

The receiving device 200 performs a predetermined process on an ultrasonic echo signal received in the transducer array TA and performs receiving beamforming. The receiving device 200 may include a received signal processor and a receiving beamformer. The electrical signal converted in the transducer array TA is input to the received signal processor. The received signal processor may amplify a signal before signal processing or time delay processing is performed on the electrical signal obtained by converting the ultrasonic echo signal, adjust a gain, or compensate for attenuation according to a depth. More specifically, the received signal processor may include a low noise amplifier (LNA) which decreases the noise of the electrical signal input from the ultrasonic transducer array TA and a variable gain amplifier (VGA) which controls a gain value according to the input signal. The VGA may utilize time gain compensation (TGC) for which a gain according to a distance from the focal point is compensated, but the present invention is not limited thereto.

The receiving beamformer performs beamforming on the electrical signal input from the received signal processor. The receiving beamformer increases the strength of the signal using a method in which the electrical signals input from the received signal processor are super-positioned. The signal that is beamformed in the receiving beamformer is converted into a digital signal through an A/D converter, and transmitted to the image processor 530 of the main device M. When the A/D converter is provided in the main device M, the analog signal beamformed in the receiving beamformer may be transmitted to the main device M and converted into the digital signal in the main device M. Also, the receiving beamformer may be a digital beamformer. The digital beamformer may include a storage in which the analog signal may be sampled and stored, a sampling period controller capable of controlling a sampling period, an amplifier capable of adjusting a size of a sample, an anti-aliasing low pass filter for preventing aliasing before sampling, a bandpass filter capable of selecting a desired frequency band, an interpolation filter capable of increasing a sampling rate when beamforming is performed, a high-pass filter capable of removing a direct current (DC) component or a signal of a low frequency band, etc.

Figure 4A:
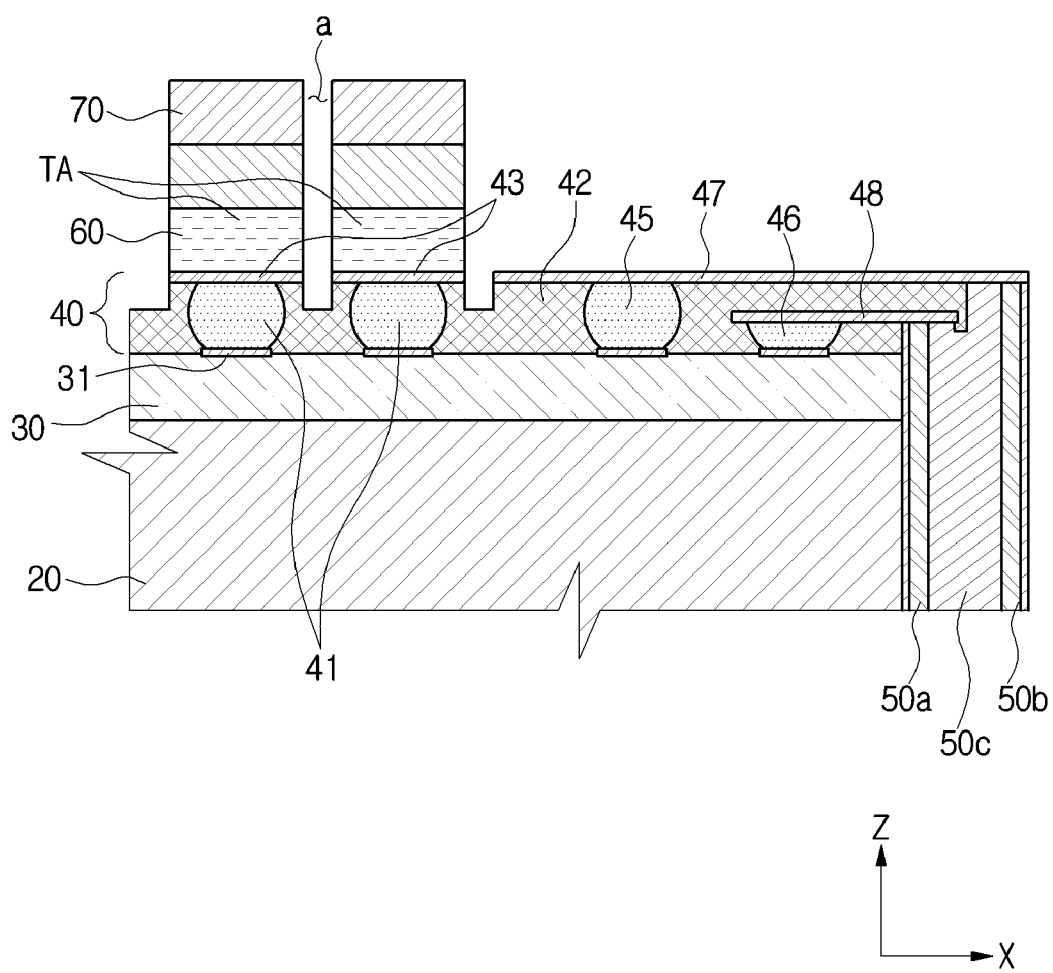
FIGS. 4A and 4B are cross-sectional views showing a structure of an ultrasonic probe according to an embodiment.
Figure 4B:
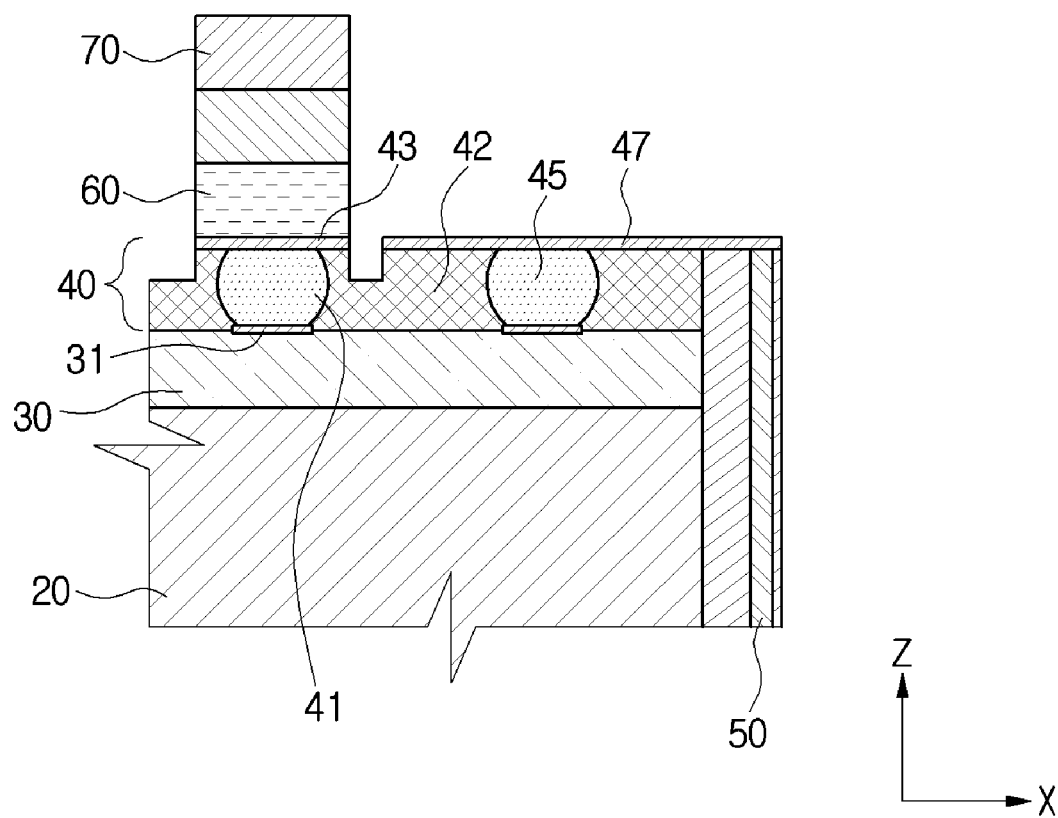
Figure 6:
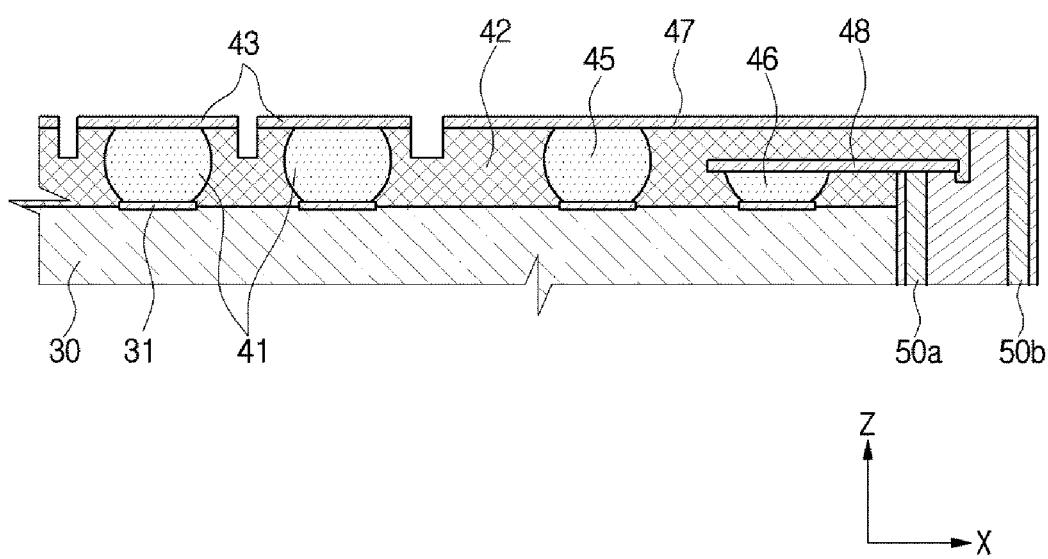
FIG. 6 is a cross-sectional view taken along line A-A' of FIG. 5.
Figure 7:
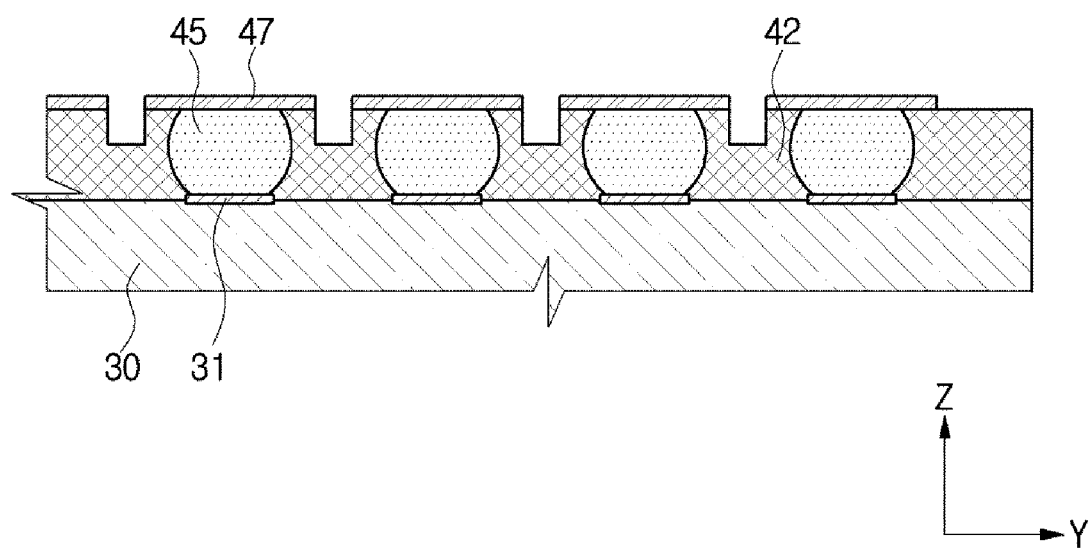
FIG. 7 is a cross-sectional view taken along line B-B' of FIG. 5.

Meanwhile, an ultrasonic probe according to an embodiment of the present invention includes a transducer module including a transducer array. Hereinafter, the transducer module will be described in detail with reference to FIGS. 4A to 7. FIGS. 4A and 4B are cross-sectional views showing a structure of an ultrasonic probe according to an embodiment of the present invention. FIG. 5 is a plan view conceptually showing a connection layer of an ultrasonic probe according to an embodiment of the present invention. FIG. 6 is a cross-sectional view taken along line A-A' of FIG. 5. FIG. 7 is a cross-sectional view taken along line B-B' of FIG. 5.

As shown in FIG. 4A, the transducer module includes the above-described transducer array TA, a first electronic circuit 30 which is provided on the back of the transducer array TA and electrically connected to the transducer array TA, a backing member 20 disposed on a back surface of the first electronic circuit 30, second electronic circuits 50a and 50b which are provided on a side surface of the first electronic circuit 30 and electrically connected to the first electronic circuit 30, and a connection layer 40 which is provided between the transducer array TA and the first electronic circuit 30 and electrically connects the transducer array TA and the second electronic circuits 50a and 50b to the first electronic circuit 30.

As shown in FIG. 4A, the backing member 20, the first electronic circuit 30, the connection layer 40, and the transducer array TA form a stacked structure in a Z-axis direction.

The backing member 20 absorbs and scatters an ultrasonic wave, which is generated in the transducer array TA and proceeds to the back thereof, to remove the ultrasonic wave, and thus may prevent image distortion. The backing member 20 may be manufactured with a plurality of layers in order to improve an attenuation effect or blocking effect of the ultrasonic wave. Although not shown in the drawing, an acoustic reflective layer capable of reflecting the ultrasonic wave, which proceeds to the back of the transducer array TA, to the front thereof may be provided between the transducer array TA and the connection layer 40. The acoustic reflective layer may be formed of a metal material such as tungsten carbide, and installed between the connection layer 40 and the transducer array TA by a non-conductive adhesive material when the acoustic reflective layer is stacked on a front surface of the connection layer 40.

A matching layer 70 may be provided on a front surface of the above-described transducer array TA. The matching layer 70 reduces a difference between acoustic impedance of the transducer array TA and acoustic impedance of the object, matches the acoustic impedance of the transducer array TA and the acoustic impedance of the object, and thus enables the ultrasonic wave generated in the transducer array TA to be efficiently delivered to the object. To this end, the matching layer 70 may be provided to have a median value of the acoustic impedance of the transducer array TA and the acoustic impedance of the object. The matching layer 70 may be formed of glass or a resin material. Also, the matching layer 70 may be formed with a plurality of layers so that the acoustic impedance may be gradually changed from the transducer array TA toward the object, and the plurality of matching layers 70 may be configured to have different materials. The matching layer 70 may be attached to the front surface of the transducer array TA by the non-conductive adhesive material.

When the transducer array TA is configured as a 2D array, the number of elements that constitute the array is greater than the number of elements that constitute a 1D array, and thus the first electronic circuit 30, for example, an ASIC, is used without connecting a signal line to each of the elements. Hereinafter, the ASIC will be exemplified to describe the first electronic circuit 30. That is, the transducer array TA is bonded to the ASIC, electric signals applied from the second electronic circuits 50a and 50b, for example, printed circuit boards (PCBs), and electric signals received from the transducer array TA are controlled according to a logic of the ASIC, and then the ultrasonic wave is transmitted and received. The second electronic circuits 50a and 50b may be formed on opposite surfaces of an electrically insulating separator 50c. Hereinafter, the PCBs will be exemplified to describe the second electronic circuits 50a and 50b. In general, a flip chip bonding method is used for bonding the transducer array TA to the ASIC. However, in this case, a crack may occur in a bonding bump or poor contact may occur between a bump of the transducer array TA and a bump of the ASIC. Since this crack or poor contact causes reduced transmission efficiency of the electrical signals, the reliability of the apparatus is degraded. In general, a wire bonding method is used for connecting the ASIC to the PCB. The wire bonding method has a problem in that the complexity of the process is increased and the footprint of the ultrasonic probe is increased. Thus, in the embodiment of the present invention, the above-described flip chip bonding method and wire bonding method are not used, and it is implemented by a new method in which the transducer array TA and the PCBs are electrically connected to the ASIC. Hereinafter, the new method will be described in detail.

As shown in FIG. 4A, the ultrasonic probe according to the embodiment of the present invention includes the connection layer 40 which electrically connects the transducer array TA to the ASIC 30. The connection layer 40 electrically connects the PCBs 50a and 50b to the ASIC 30 as well as connecting the transducer array TA to the ASIC 30.

The connection layer 40 includes a first conductor array 41 having an array corresponding to the transducer array TA and a non-conductive material 42 which fills spaces around the first conductor array 41. The non-conductive material 42 fills spaces around a second conductor array 45 and 46 to be described below as well as those of the first conductor array 41. A part of the first conductor array 41 having a 2D array is shown in FIG. 5. For example, when the transducer array TA has a size of 64×128, the first conductor array 41 included in the connection layer 40 is also provided to have a size of 64×128. The transducer array according to the embodiment of the present invention and the first conductor array have the form of a 2D array, but the forms of the transducer array and the first conductor array are not limited to the 2D array. That is, as shown in FIG. 4B, the structure of the ultrasonic probe according to the embodiment of the present invention may be applied to the case in which the transducer array and the first conductor array have the form of the 1D array and also the case in which only one element is included without configuring the array.

Therefore, as shown in FIG. 4A, each of conductors that constitute the first conductor array 41 is in contact with each of the elements 60 that constitute the transducer array TA in a one-to-one correspondence. The first conductor array 41 is in contact with pads 31 provided in the ASIC 30 and the transducer array TA, and thus electrically connects the transducer array TA to the ASIC 30. Although the conductor is illustrated as a spherical shape in the drawing, it is a simple example, and it may also be provided in other various shapes. The connection layer 40 according to the embodiment of the present invention includes first electrodes 43 provided on a front surface of the conductor so that a contact area between each of the conductors that constitute the first conductor array 41 and the transducer element 60 may be increased. When the first conductor array 41 and the transducer array TA are in contact with each other without the first electrode 43, the conductor is only in contact with a partial area of the transducer element 60. However, as described in the embodiment of the present invention, when the first electrode 43 having the same area as the transducer element 60 is formed on the front surface of the conductor, the first electrode 43 is in contact with the entire area of the transducer element 60, and thus the efficiency of the electrical signal transmission is increased. The first electrode 43 may be formed on a front surface of the connection layer 40 including the first conductor array 41 using a deposition method, a sputtering method, a plating method, or a spray method to have a thickness in a range from 0.1 μm to 0.5 μm. When the first electrode 43 is formed and then the transducer is stacked on the front surface of the connection layer 40, the transducer is divided into a 2D array by a dicing process. In this case, since the dicing process is performed to a predetermined depth of the connection layer 40, the first electrode 43 is divided together with the transducer and has the same shape and area as the transducer element 60. In FIG. 4A, a gap a between the transducer element 60 and the element 60 which are divided by the dicing process is illustrated. Then, it may be seen that the dicing process is performed to a predetermined depth of the connection layer 40, the first electrode 43 is separated, and the transducer element 60 and the first electrode 43 have the same shape and area. The first electrode 43 may be formed of a highly conductive metal such as gold, silver, copper, or a combination thereof. Meanwhile, when the transducer is stacked, the transducer may be attached to a front surface of the first electrode 43 by a non-conductive adhesive material.

The connection layer 40 further includes a second conductor array 45 and 46, which electrically connect the PCBs 50a and 50b to the ASIC 30, therein. The second conductor array 45 and 46 may be arranged in two columns as shown in FIGS. 4A and 5, but it is a simple example, the second conductor array 45 and 46 may be arranged in one column as shown in FIG. 4B or may be configured of one conductor. The number of PCBs 50a and 50b mounted on side surfaces of the backing member 20 may be the same as the number of columns of the second conductor array 45 and 46. For example, as shown in FIGS. 4A, 5, and 6, the connection layer 40 may include two columns of the second conductor array 45 and 46, and two columns of the PCBs 50a and 50b may be mounted on the side surfaces of the backing member 20. As shown in FIG. 4B, when the second conductor array 45 and 46 are arranged in one column or configured of one conductor, one PCB 50 may be mounted on the side surface of the backing member 20 unlike FIG. 4A.

The PCBs 50a and 50b mounted on the side surface of the backing member 20 may be attached to the side surface of the backing member 20 by a non-conductive adhesive material. The columns 45 and 46 that constitute the second conductor array are each connected to the different PCBs 50a and 50b through the second and third electrodes 47 and 48. As shown in FIGS. 4A, 5, and 6, the conductors that constitute a right-side column 46 of the second conductor array 45 and 46 are connected to the left-side PCB 50a, the conductors that constitute a left-side column 45 of the second conductor array 45 and 46 are connected to the right-side PCB 50b. The columns 45 and 46 of the second conductor arrays are each connected to the PCBs 50a and 50b through the second and third electrodes 47 and 48. In order to prevent the second and third electrodes 47 and 48 from being in contact with each other, as shown in FIGS. 4A and 6, the second and third electrodes 47 and 48 are spaced apart from each other in a Z-axis direction to form different layers. As shown in FIGS. 4A and 6, a cutting 49 exists between the right-side PCB 50b and the third electrode 48 that is connected to the left-side PCB 50*a*. The cutting 49 prevents the third electrode 48 from being electrically connected to the right-side PCB 50*b*. An arrangement of the second and third electrodes 47 and 48 of the second conductor array 45 and 46 shown in FIGS. 4A and 6 will be described in more detail through the description of a manufacturing process to be described below.

The second and third electrodes 47 and 48 of the second conductor array 45 and 46 may also be formed on the front surface of the connection layer 40 including the second conductor array 45 and 46 using a deposition method, a sputtering method, a plating method, or a spray method in the same manner as the first electrode 43 of the first conductor array 41 to have a thickness in a range from 0.1 μm to 0.5 μm. When the second and third electrodes 47 and 48 are formed and then the transducer is stacked on the front surface of the connection layer 40, the transducer is divided into a 2D array by a dicing process. In this case, the second and third electrodes 47 and 48 of the second conductor array 45 and 46 are separated from each other in a Y-axis direction by the dicing process according to an X-axis direction as shown in FIG. 7. Then, the first electrode 43 of the first conductor array 41 and the second and third electrodes 47 and 48 of the second conductor array 45 and 46 are separated from each other by the dicing process according to the Y-axis direction as shown in FIG. 6. The second and third electrodes 47 and 48 may be formed of a highly conductive metal such as gold, silver, copper, or a combination thereof.

As described above, the ultrasonic probe according to the embodiment of the present invention includes the connection layer 40 including the first conductor array 41 being in contact with the transducer array TA and the second conductor array 45 and 46 being in contact with the PCBs 50*a* and 50*b* therein, and may electrically connect the transducer array TA and the PCBs 50*a* and 50*b* to the ASIC 30 without using a flip chip bonding method or a wire bonding method. Since the ultrasonic probe according to the embodiment of the present invention does not use the flip chip bonding method or the wire bonding method, the problem due to cracks of the bump or poor contact, and the problem such as increasing of the complexity of the process can be addressed.

Figure 8:
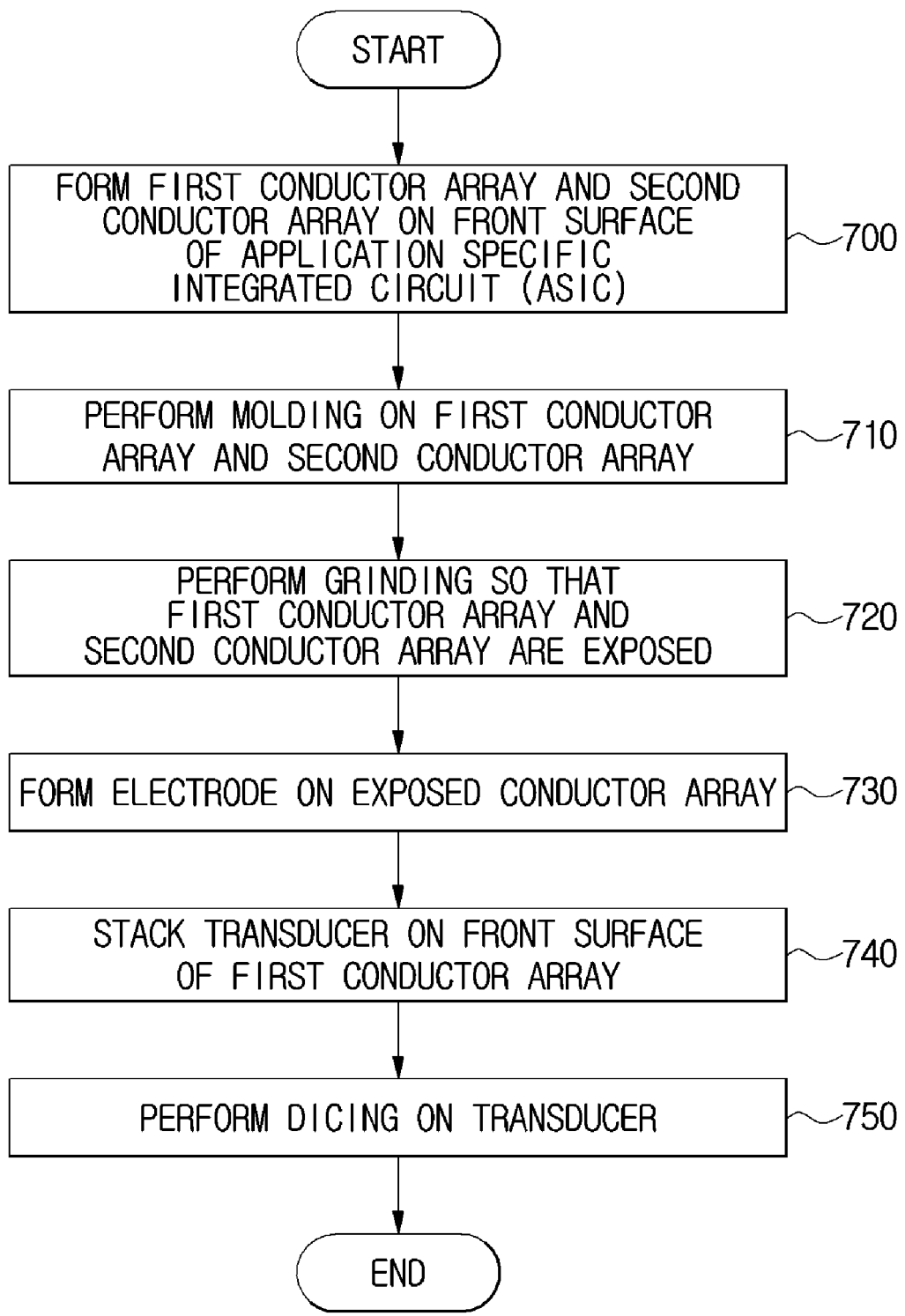
FIG. 8 is a flowchart showing a method of manufacturing an ultrasonic probe according to an embodiment of the present invention.

FIG. 8 is a flowchart showing a method of manufacturing an ultrasonic probe according to an embodiment of the present invention.

As shown in FIG. 8, a first conductor array 41 and second conductor array 45 and 46 are formed on a front surface of an ASIC 30 provided on a front surface of a backing member 20 (700). The ASIC 30 may be attached to the front surface of the backing member 20 by a non-conductive adhesive material. The first conductor array 41 is formed to have a size corresponding to a size of a transducer array TA, and the second conductor array 45 and 46 are formed in at least one column. As shown in FIGS. 4A, 5, and 6, according to the embodiment of the present invention, the second conductor array may be formed in two columns 45 and 46. In a part of the stacked structure inside the ultrasonic probe illustrated in FIGS. 4A, 5, and 6, when looked at in a view of a whole of the stacked structure, the first conductor array 41 may be formed at a center of the ASIC 30, and the second conductor array 45 and 46 may be formed on both sides thereof. Of course, the second conductor array 45 and 46 may be formed on only one side of the first conductor array 41. Although the conductor may have a form of a spherical bump implemented as a conductive material, it is not limited thereto and it may be implemented in various forms. The first conductor array 41 and the second conductor array 45 and 46 are in contact with pads 31 of the ASIC 30 and electrically connected to the ASIC 30.

When the first conductor array 41 and the second conductor array 45 and 46 are formed on the ASIC 30, a molding process is performed on the first conductor array 41 and the second conductor array 45 and 46 (710). When the first conductor array 41 and the second conductor array 45 and 46 are formed, the molding process is performed on the first conductor array 41 and the second conductor array 45 and 46 with a non-conductive material. In FIG. 4A, the PCBs 50*a* and 50*b* are installed on side surfaces of the backing member 20 and the ASIC 30, but it is preferable that the PCBs 50*a* and 50*b* be installed before a grinding process to be described below. For example, the PCBs 50*a* and 50*b* may be installed on the side surfaces of the ASIC 30 after the molding process is performed on the first conductor array 41 and the second conductor array 45 and 46 or before the molding process. The PCBs 50*a* and 50*b* are installed either on both side surfaces of the ASIC 30 or on any one side surface thereof. It is preferable that the PCBs 50*a* and 50*b* be installed on side surfaces adjacent to the second conductor array 45 and 46.

Alternatively, the PCBs 50*a* and 50*b* may be installed before the first conductor array 41 and the second conductor array 45 and 46 are installed. When the PCBs 50*a* and 50*b* are installed first, the second conductor array 45 and 46 may be installed adjacent to the PCBs 50*a* and 50*b*.

When the first conductor array 41 and the second conductor array 45 and 46 are molded, a grinding process is performed on the molding to expose the first conductor array 41 and the second conductor array 45 and 46 (720), and electrodes are formed on the exposed first conductor array 41 and second conductor array 45 and 46 (730). FIGS. 9A-9D are cross-sectional views conceptually showing a process of forming an electrode on a conductor array included in a connection layer of an ultrasonic probe according to an embodiment of the present invention. FIGS. 10A-10D are cross-sectional views conceptually showing a process of forming an electrode when a second conductor array configured in a single column is included in a connection layer of an ultrasonic probe according to an embodiment of the present invention. FIGS. 11A-11H are cross-sectional views conceptually showing a process of forming an electrode when a second conductor array configured in two columns is included in a connection layer of an ultrasonic probe according to an embodiment of the present invention.

The case in which the second conductor array is configured in a single column and the case in which the second conductor array is configured in two columns have slightly different electrode forming processes. Thus, hereinafter, the case in which the second conductor array is configured in a single column will be described first, and then the case in which the second conductor array is configured in two columns will be described.

Referring to FIGS. 9A-9D, the process of forming the electrode on the conductor array includes a grinding process and a sputtering process. When the conductor array is molded, the grinding process is performed so that the conductor array may be exposed on a front surface of the molding. The grinding process may be performed so that a conductor and a non-conductive material may be formed to have the same height as shown in FIG. 9C. The grinding process may be performed using various known methods. When the conductor array is exposed by the grinding process, the electrode is formed on the exposed conductor array using a deposition method, a sputtering method, a plating method, or a spray method. As shown in FIG. 9D, according to the embodiment of the present invention, the electrode is also formed on the non-conductive material portion as well as the exposed conductor portion, and thus an electrical contact area may be widely formed. When the electrode is widely formed as shown in FIG. 9D to be in electrical contact with the transducer, electrical resistance may be reduced and thus transmission efficiency of the electrical signal can be improved, and thus the quality of the ultrasonic image can be improved. Also, when the electrode is widely formed as shown in FIG. 9D, physical bonding of the connection layer and the transducer can be improved and a structure of the ultrasonic probe can become even more robust.

In this case, it is preferable that the electrode be formed to have a thickness in a range from 0.1 μm to 0.5 μm.

As shown in FIGS. 10A-10D, when the second conductor array is configured in a single column, a grinding process is performed on the molding to expose all of the first conductor array 41 and the second conductor array 45 and 46 as described above. When the first conductor array 41 and the second conductor array 45 and 46 are exposed, electrodes are formed on the PCBs as well as the first conductor array 41 and the second conductor array 45 and 46 so that the exposed first conductor array 41 and the PCBs may be electrically connected to the PCBs. In the case in which the second conductor array is configured in a single column, as described above, the formation of the electrode on the first conductor array 41 and the second conductor array 45 and 46 may be completed by only a single electrode forming process.

As shown in FIGS. 11A-11H, when the second conductor array is configured in two columns, a grinding process is performed to expose the second conductor array in the column 46 which is selected from the second conductor array 45 and 46 and close to the PCB 50a. More specifically, as shown in FIG. 11C, the grinding process is performed on one column 46 of the second conductor array 45 and 46 and the PCB 50a to be electrically connected thereto. As shown in FIG. 11D, when the grinding process has been performed, the third electrode 48 is formed on a portion on which the grinding process has been performed. The third electrode 48 formed as described above electrically connects one column 46 of the second conductor array 45 and 46 to the PCB 50a in one column adjacent thereto. When the third electrode 48 has been formed, an end of the third electrode 48 on a side of the PCB 50a is cut as shown in FIG. 11E, the third electrode 48 is separated from the other PCB 50b, and thus the third electrode 48 is prevented from being electrically connected to the other PCB 50b. When the third electrode 48 has been separated, the third electrode 48 is molded again as shown in FIG. 11F, and then the grinding process is performed to expose the other second conductor array 45 as shown in FIG. 11G. When the other second conductor array 45 has been exposed by performing the grinding process, the second electrode 47 is formed in order to electrically connect the other second conductor array 45 to the other PCB 50b as shown in FIG. 11H. The second electrode 47 formed as described above electrically connects the second conductor array 45 in the other column to the other PCB 50b. When the second and third electrodes 47 and 48 are formed as described above, as shown in FIG. 11H, the second and third electrodes 47 and 48 are physically spaced apart from each other by the molding which fills between the second and third electrodes 47 and 48, formed to be different layers, and thus also electrically separated. The process shown in FIGS. 10A-10D is a simple example, and a process for preventing the second and third electrodes 47 and 48 which connect the second conductor array 45 and 46 configured in multiple columns to the PCBs 50a and 50b from being in contact with each other can be seen to be included in the scope of the embodiment of the present inventions.

When the electrode is formed, the transducer is stacked on a front surface of the first conductor array 41 (740), a dicing process is performed on the stacked transducer, and then the transducer array TA is formed (750).

When the electrode is formed, the transducer is stacked on the front surface of the first conductor array 41. The transducer is stacked, and then the matching layer 70 may be stacked on a front surface of the transducer, or the transducer in which the matching layer 70 is already stacked on the front surface thereof may be stacked on the front surface of the first conductor array 41.

When the transducer is stacked, the transducer is diced in order to produce a 2D transducer array TA having a desired size. When the dicing process is performed, the dicing process is performed on the molding portion including the first conductor array 41 as well as the transducer to a predetermined depth, and thus the first electrode 43 formed on the front surface of the first conductor array 41 is divided together with the transducer. That is, after the dicing process is performed, as shown in FIG. 4A, the first electrode 43 formed on the front surface of the first conductor array 41 also forms an array to have the same size as the first conductor array 41 and the transducer array TA, and the first electrodes 43 that constitute the array are electrically separated from each other. Also, the first electrode 43 is diced with the transducer, and thus has the same area and form as the elements 60 that constitute the transducer array TA. An entire area of the first electrode 43 is in contact with an entire area of the transducer element 60, and thus electrical signal transmission efficiency between the transducer element 60 and the conductor mediated by the first electrode 43 is increased. When the conductor is in direct contact with the transducer element 60 without the first electrode 43, a contact area between the transducer element 60 and the conductor is smaller than a contact area between the first electrode 43 and the transducer element 60, and thus the transmission efficiency of the electrical signal is reduced.

The dicing process on the transducer is performed along X and Y axes, and the dicing process is performed on an area corresponding to the second conductor array 45 and 46 as well as an area corresponding to the first conductor array 41 when the dicing process is performed in the X-axis direction. Thus, the second and third electrodes 47 and 48 formed on the front surface of the second conductor array 45 and 46 are separated in the Y-axis direction as shown in FIG. 7. When the dicing process is performed in the Y-axis direction, the dicing process is performed between the first conductor array 41 and the second conductor array 45 and 46, and thus the first electrode 43 of the first conductor array 41 and the second and third electrodes 47 and 48 of the second conductor array 45 and 46 may be separated as shown in FIG. 6. In other words, the second and third electrodes 47 and 48 of the second conductor array 45 and 46 are separated by the dicing process performed in the X-axis direction as shown in FIG. 7, and the first electrode 43 of the first conductor array 41 and the second and third electrodes 47 and 48 of the second conductor array 45 and 46 are separated by the dicing process performed in the Y-axis direction as shown in FIG. 6.

As is apparent from the above description, the ultrasonic probe can be manufactured without a flip chip bonding method or a wire bonding method, and thus manufacturing time and costs can be reduced.

Also, the tolerance of the flatness of the ASIC is reduced, and thus the performance of the ultrasonic probe can be improved.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic probe comprising:
an ultrasonic transducer configured to transmit and receive an ultrasonic wave;
a first electronic circuit electrically connected to the ultrasonic transducer;
second electronic circuits each electrically connected to the first electronic circuit;
a connection layer including a first conductor disposed between the ultrasonic transducer and the first electronic circuit so that the ultrasonic transducer is electrically connected to the first electronic circuit, and a second conductor disposed on one surface of the first electronic circuit so that the second electronic circuits are electrically connected to the first electronic circuit; and
an electrode disposed on a front surface of the connection layer to be in contact with the first conductor, the ultrasonic transducer, the second conductor and the second electronic circuits.

2. The ultrasonic probe according to claim 1, wherein:
the second electronic circuits are disposed on a surface adjacent to the second conductor among side surfaces of the first electronic circuit,
the second conductor includes a plurality of columns formed in a direction parallel to the second electronic circuits, and
an electrode configured to connect any one column of the second conductor to any one second electronic circuit, and an electrode configured to connect another column of the second conductor to another second electronic circuit, are spaced apart from each other.

3. The ultrasonic probe according to claim 2, wherein the plurality of columns of the second conductor are formed in the same layer.

4. The ultrasonic probe according to claim 2, wherein the electrode configured to connect any one column of the second conductor to any one second electronic circuit, and the electrode configured to connect another column of the second conductor to another second electronic circuit, are formed in different layers.

5. The ultrasonic probe according to claim 1, wherein an area of the electrode is provided to correspond to an area of the ultrasonic transducer being in contact with the electrode.

6. The ultrasonic probe according to claim 1, wherein the first conductor and the second conductor are formed in the same layer.

7. The ultrasonic probe according to claim 1, wherein at least one of the first electronic circuit and the second electronic circuits includes a semiconductor device (an application specific integrated circuit (ASIC)).

8. The ultrasonic probe according to claim 1, wherein:
the connection layer is disposed on a back surface of the ultrasonic transducer;
the first electronic circuit is disposed on a back surface of the connection layer; and
the second electronic circuits are disposed on a side surface of the first electronic circuit.

9. The ultrasonic probe according to claim 1, wherein the ultrasonic transducer is formed in an array form including a plurality of ultrasonic elements and the first conductor is formed in an array form including a plurality of conductors.

10. The ultrasonic probe according to claim 1, wherein the connection layer includes a non-conductive material configured to embed the first conductor and the second conductor.

11. An ultrasonic probe comprising:
an ultrasonic transducer configured to transmit and receive an ultrasonic wave;
a connection layer disposed on a back surface of the ultrasonic transducer and electrically connected to the ultrasonic transducer;
a first electronic circuit disposed on a back surface of the connection layer to be electrically connected to the connection layer; and
a second electronic circuit disposed on a side surface of the first electronic circuit to be electrically connected to the first electronic circuit,
wherein the connection layer comprises:
a first conductor disposed between the ultrasonic transducer and the first electronic circuit so that the ultrasonic transducer is electrically connected to the first electronic circuit; and
a second conductor disposed on a front surface of the first electronic circuit so that the first electronic circuit is electrically connected to the second electronic circuit; and an electrode disposed on a front surface of the connection layer to be in contact with the first conductor, the ultrasonic transducer, the second conductor and the second electronic circuit.

12. An ultrasonic probe comprising:
an ultrasonic transducer configured to transmit and receive an ultrasonic wave;
a first conductor disposed on a back surface of the ultrasonic transducer;
a first electrode disposed between the ultrasonic transducer and the first conductor so that the ultrasonic transducer is electrically connected to the first conductor;
a first electronic circuit disposed on a back surface of the first conductor to be electrically connected to the first conductor;
a second conductor disposed on a front surface of the first electronic circuit to be electrically connected to the first electronic circuit;
a second electrode disposed on a front surface of the second conductor; and
a second electronic circuit disposed on a side surface of the first electronic circuit and electrically connected to the second electrode; wherein the first electrode is disposed on a front surface of the first conductor to be in contact with the first conductor and the ultrasonic transducer, and the second electrode is in contact with the second conductor and the second electronic circuit.

13. An ultrasonic probe comprising:
an ultrasonic transducer configured to transmit and receive an ultrasonic wave;
a first electronic circuit electrically connected to the ultrasonic transducer;
a connection layer disposed between the ultrasonic transducer and the first electronic circuit so that the ultrasonic transducer is electrically connected to the first electronic circuit; and an electrode disposed on a front surface of the connection layer to be in contact with a first conductor and the ultrasonic transducer.

14. The ultrasonic probe according to claim 13, wherein the first electronic circuit includes a semiconductor device (ASIC).

15. An ultrasonic probe comprising:
an ultrasonic transducer configured to transmit and receive an ultrasonic wave;
a first electronic circuit electrically connected to the ultrasonic transducer;
a connection layer disposed between the ultrasonic transducer and the first electronic circuit;
second electronic circuits each disposed on a side surface of the first electronic circuit to be electrically connected to the first electronic circuit; and
an electrode disposed on a front surface of the connection layer to be in contact with the second conductor and the second electronic circuits,
wherein the connection layer includes a second conductor disposed on a front surface of the first electronic circuit so that the second electronic circuits are electrically connected to the first electronic circuit.

16. The ultrasonic probe according to claim 15, wherein:
the second electronic circuits are disposed on a surface adjacent to the second conductor among side surfaces of the first electronic circuit,
the second conductor includes a plurality of columns formed in a direction parallel to the second electronic circuits, and
an electrode configured to connect any one column of the second conductor to any one second electronic circuit, and an electrode configured to connect another column of the second conductor to another second electronic circuit, are spaced apart from each other.

17. The ultrasonic probe according to claim 16, wherein the plurality of columns of the second conductor are formed in the same layer.

18. The ultrasonic probe according to claim 16, wherein the electrode configured to connect any one column of the second conductor to any one second electronic circuit, and the electrode configured to connect another column of the second conductor to another second electronic circuit, are formed in different layers.

19. A method of manufacturing an ultrasonic probe, comprising:
forming a conductor array on one surface of a first electronic circuit;
forming a molding in a space including the conductor array;
performing a grinding process on the molding to expose the conductor array;
forming an electrode on a surface on which the grinding process is performed; and
stacking an ultrasonic transducer on the electrode,
wherein the electrode is disposed on a front surface of a connection layer to be in contact with the conductor array, the ultrasonic transducer, a second conductor and a second electronic circuit.

20. The method according to claim 19, further comprising performing a dicing process on the ultrasonic transducer and the molding so that the ultrasonic transducer is formed as a 2-dimensional (2D) array.

21. The method according to claim 19, wherein the forming of the electrode includes forming an electrode on the exposed conductor array and the molding therearound through a sputtering method or a plating method.

22. The method according to claim 19, further comprising installing at least one second electronic circuit on one side surface of the first electronic circuit,
wherein the forming of the conductor array includes forming a first conductor array connected to the ultrasonic transducer and a second conductor array connected to the at least one second electronic circuit.

23. The method according to claim 22, wherein the forming of the electrode includes forming an electrode on the exposed first conductor array and second conductor array, the molding around the first and second conductor arrays, and the at least one second electronic circuit through a sputtering method.

24. The method according to claim 23, further comprising:
when the ultrasonic transducer is stacked on the electrode formed on the first conductor array, dicing the ultrasonic transducer and the molding in a direction perpendicular to the second electronic circuit; and
dicing the ultrasonic transducer and the molding corresponding to the ultrasonic transducer in a direction perpendicular to the dicing direction and generating a 2D array ultrasonic transducer.

25. The method according to claim 22, wherein the second conductor array includes a plurality of columns formed in a direction parallel to the at least one second electronic circuit,
wherein the performing of the grinding process further comprises performing a grinding process on the molding corresponding to any one column of the plurality of columns of the second conductor array and any one second electronic circuit among the at least one second electronic circuit, and
wherein the forming of the electrode includes forming an electrode on a surface on which the grinding process is performed through a sputtering method so that any one column of the second conductor array exposed by performing the grinding process is electrically connected to the second electronic circuit.

26. The method according to claim 25, further comprising:
cutting an end of the formed electrode at a side of the second electronic circuit in order to prevent the formed electrode and another electronic circuit from being electrically connected;
remolding the electrode;
further performing a grinding process on the molding corresponding to another column so that another column of the plurality of columns of the second conductor array is further exposed; and
further forming an electrode on a surface on which the grinding process is further performed through a sputtering method so that another column of the plurality of columns of the second conductor array is electrically connected to another second electronic circuit of the at least one second electronic circuit.

27. An ultrasonic probe comprising:
an ultrasonic transducer including one or more ultrasonic transducer elements;
a first electronic circuit including one or more pads that correspond to the one or more ultrasonic transducer elements and extend along a first direction;
a connection layer interposed between the ultrasonic transducer and the first electronic circuit, and including one or more first conductors electrically connecting the one or more ultrasonic transducer elements and the one or more pads to each other and an electrically insulating layer filling spaces around the one or more first conductors; and a second electronic circuit disposed on a side surface of the first electronic circuit by extending along a second direction intersected by the first direction, and electrically connected to the first electronic circuit via an electrode extending along the first direction, wherein the electrode is disposed on a front surface of the connection layer to be in contact with the first conductor, the ultrasonic transducer, the second conductor and the second electronic circuit.

28. The ultrasonic probe of claim 27, further comprising one or more first electrodes interposed between the one or more first conductors and the one or more ultrasonic transducer elements.

29. The ultrasonic probe of claim 28, wherein the electrically insulating layer has one or more grooves adjacent to the one or more first conductors, wherein a side wall of each groove is coplanar with side surfaces of one first electrode and one ultrasonic transducer element.

30. The ultrasonic probe of claim 27, wherein the electrode, via which the first electronic circuit and the second electronic circuit are electrically connected to each other, is coplanar with the one or more first electrodes.

31. The ultrasonic probe of claim 27, further comprising an embedded electrode embedded within the electrically insulating layer of the connection layer, wherein the second electronic circuit includes an electrically insulating separator and first and second electronic layers that are disposed on opposite surfaces of the electrically insulating separator and that are electrically connected to the electrode and the embedded electrode, respectively.

32. The ultrasonic probe of claim 31, wherein the first and second electronic layers of the second electronic circuit are printed circuit boards.

33. The ultrasonic probe of claim 27, wherein at least one of the first electronic circuit and the second electronic circuit is a semiconductor chip.

* * * * *